US011029297B2

(12) United States Patent
Ye (10) Patent No.: US 11,029,297 B2
(45) Date of Patent: Jun. 8, 2021

(54) METHOD OF GAS COMPOSITION DETERMINATION, ADJUSTMENT, AND USAGE

(71) Applicant: Applied Materials, Inc., Santa Clara, CA (US)

(72) Inventor: Zhiyuan Ye, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 193 days.

(21) Appl. No.: 16/449,045

(22) Filed: Jun. 21, 2019

(65) Prior Publication Data

US 2020/0049676 A1 Feb. 13, 2020

Related U.S. Application Data

(60) Provisional application No. 62/715,855, filed on Aug. 8, 2018.

(51) Int. Cl.
*G01N 33/00* (2006.01)
*G01N 29/036* (2006.01)

(52) U.S. Cl.
CPC ......... *G01N 33/005* (2013.01); *G01N 29/036* (2013.01); *G01N 33/0062* (2013.01);
(Continued)

(58) Field of Classification Search
CPC ..... G01N 2033/0068; G01N 2291/014; G01N 2291/021; G01N 2291/0215;
(Continued)

(56) References Cited

U.S. PATENT DOCUMENTS 3,434,334 A * 3/1969 Vandenbussche ....... G01H 3/00
73/24.01
5,386,714 A * 2/1995 Dames ................... G01N 9/002
73/24.05
(Continued)

FOREIGN PATENT DOCUMENTS

SE 44596 A1 * 1/1982
WO 2008026146 A1 3/2008

OTHER PUBLICATIONS

International Search Report and Written Opinion dated Oct. 18, 2019 for Application No. PCT/US2019/038582.

*Primary Examiner* — Francis C Gray
(74) *Attorney, Agent, or Firm* — Patterson + Sheridan, LLP (57) ABSTRACT

Methods and systems for determining concentrations of gases within a process chamber are provided. In one or more embodiments, a method includes introducing a first gas into a first cavity of a gas monitoring module, where the first cavity is thermally coupled to a second cavity of the gas monitoring module, and where the first cavity contains a first inlet and the first gas is introduced via the first inlet. The method includes introducing a gas mixture containing the first gas and a second gas into a second cavity, where the second cavity contains a second inlet and the gas mixture is introduced via the second inlet. The method also includes determining a first speed of sound inside the first cavity, determining a second speed of sound inside the second cavity, and determining a concentration of the second gas in the second cavity based on the first and second speeds of sound.

20 Claims, 4 Drawing Sheets

(52) U.S. Cl.
CPC .............. *G01N 2033/0068* (2013.01); *G01N 2291/014* (2013.01); *G01N 2291/0215* (2013.01)

(58) Field of Classification Search
CPC ....... G01N 2291/02809; G01N 29/024; G01N 29/036; G01N 29/22; G01N 29/4472; G01N 33/005; G01N 33/0062
See application file for complete search history.

(56) References Cited

U.S. PATENT DOCUMENTS

| | | | |
|---|---|---|---|
| 6,634,214 B1 * | 10/2003 | Thurston | G01N 9/24 73/32 A |
| 8,475,715 B2 * | 7/2013 | Masters | G01N 29/036 422/82 |
| 9,818,850 B2 | 11/2017 | Yamazaki | |
| 10,373,822 B2 | 8/2019 | Kulshreshtha et al. | |
| 10,388,549 B2 | 8/2019 | Paul et al. | |
| 2002/0062681 A1 * | 5/2002 | Livingston | G01N 29/326 73/24.01 |
| 2007/0220976 A1 * | 9/2007 | Ewerlin | G01N 29/222 73/579 |
| 2010/0011836 A1 | 1/2010 | Kalkman et al. | |
| 2010/0281949 A1 | 11/2010 | Cardelius | |
| 2012/0000490 A1 | 1/2012 | Chung et al. | |
| 2013/0125622 A1 | 5/2013 | Wajid | |
| 2013/0344625 A1 | 12/2013 | Benvegnu et al. | |
| 2014/0238438 A1 | 8/2014 | Segev et al. | |
| 2015/0364390 A1 | 12/2015 | Benvegnu et al. | |
| 2017/0125313 A1 | 5/2017 | Benvegnu et al. | |

* cited by examiner

METHOD OF GAS COMPOSITION DETERMINATION, ADJUSTMENT, AND USAGE

CROSS-REFERENCE TO RELATED APPLICATIONS

This application claims benefit to U.S. Appl. No. 62/715,855, filed on Aug. 8, 2018, which is herein incorporated by reference.

BACKGROUND

Field

Embodiments of the present disclosure generally relate to the chemical delivery and control for substrate process chambers.

Description of the Related Art

Gas concentrations of one or more gases in a vessel are measured for a variety of purposes, including substrate and component processing as well as maintenance and cleaning. A concentration of one or more gases in a mixture may be determined by various methods including mass spectrometry, Fourier transformation infrared spectroscopy (FTIR), gas analyzers such as side stream analyzers, refractometry, piezoelectric absorption, and Raman scattering. However, existing methods are expensive, time consuming, or utilize variables in calculations that are not available or are not easily determined from the system where the gas concentration is to be measured, or require calibration periodically. Errors in these measurements may result in costly adjustments to the composition, or in an incorrect composition being used for various applications.

Thus, there exists a need for an improved method and system for determining gas compositions.

SUMMARY

Embodiments of the present disclosure generally relate to methods and systems for determining concentrations of gases within a process chamber. In one or more embodiments, a method of determining a gas composition in a process chamber includes introducing a first gas into a first cavity of a gas monitoring module, where the first cavity of the gas monitoring module is thermally coupled to a second cavity of the gas monitoring module, and where the first cavity contains a first outlet and a first inlet and the first gas is introduced via the first inlet. The method also includes introducing a gas mixture containing the first gas and a second gas into a second cavity of the gas monitoring module, where the second cavity contains a second inlet and a second outlet and the gas mixture is introduced via the second inlet. The method further includes determining a first speed of sound inside the first cavity, determining a second speed of sound inside the second cavity, and determining a concentration of the second gas in the second cavity based on the first speed of sound and the second speed of sound.

In other embodiments, a method of determining a gas composition in a process chamber includes coupling a device to a process chamber, where a first cavity of the device is thermally coupled to a second cavity of the device and the first cavity and second cavity are at a first temperature, and where the first cavity contains a first outlet and a first inlet and the second cavity contains a second outlet and a second inlet. The method also includes introducing a first gas into the first cavity via the first inlet, introducing a gas mixture containing the first gas and a second gas into the second cavity via the second inlet, determining a first difference between a frequency of a first harmonic and a frequency of the second harmonic of the first gas, and determining a second difference between a frequency of a first harmonic and a frequency of the second harmonic of the gas mixture. The method further includes determining a concentration of the second gas in the second cavity based on a ratio of the first difference to the second difference.

In some embodiments, a system contains a gas monitoring module containing an outside wall and an interior wall, where the interior wall forms a first cavity having a first inlet and a first outlet and a second cavity of the gas monitoring module containing a second inlet and a second outlet, and where the first cavity and the second cavity are thermally coupled. The system also contains a first thermocouple associated with the first cavity and a second thermocouple associated with the second cavity.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, as the disclosure may admit to other equally effective embodiments.

DETAILED DESCRIPTION

Embodiments of the present disclosure are directed towards determining a composition of a gas mixture. In one or more examples, as the gas mixture is a binary gas mixture. The composition of the gas mixture is determined prior to releasing the gas mixture into a process chamber, or determined during a continuous flow of the gas mixture into the process chamber. The composition of the gas mixture is determined by speed of sound, using time of flight or frequencies and sound resonance. That is, composition of the gas mixture is determined by determining a speed of sound in a gas monitoring module coupled to the process chamber. The gas mixture composition is determined by optionally measuring a length of a first cavity with a known gas composition, and, subsequently, determining a composition of a gas mixture within a second cavity. The gas mixture in the second cavity includes the gas in the first cavity of the gas monitoring module. Based upon the frequency analysis of the gas monitoring module, a concentration of the second gas in the gas mixture is calculated. The concentration of gases in the gas mixture in the second cavity is then either adjusted and/or released into the process chamber based upon the concentration determined using the methods discussed herein. In embodiments where there is a continuous flow of the gas mixture from the second cavity into the process chamber during testing, the continuous flow of the gas mixture is adjusted based upon the concentration determination as discussed below. In some examples, where there is a continuous flow of the gas mixture from the second cavity into the process chamber during testing, a concentration of the gas mixture is adjusted based upon the concentration determination.

Figure 1:
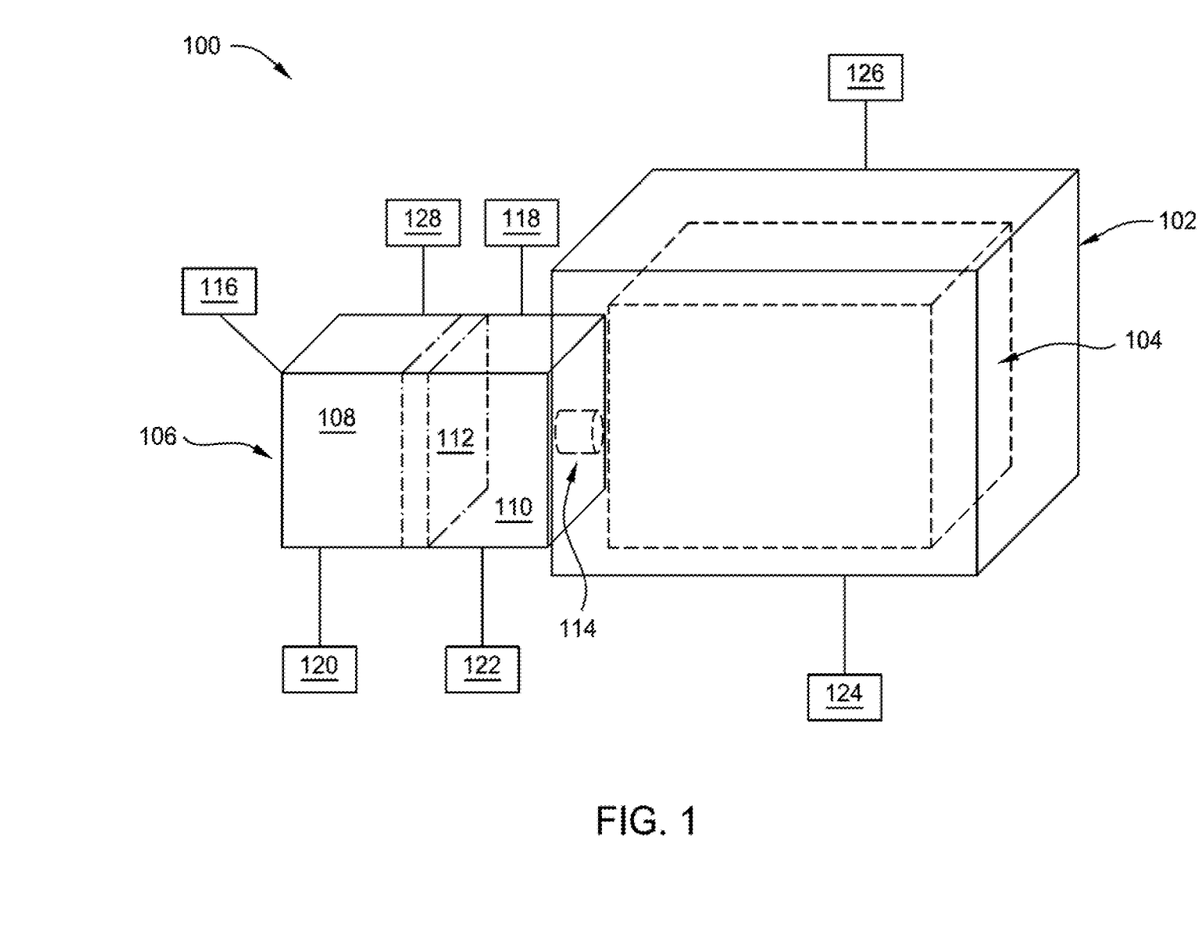
FIG. 1 shows a schematic illustration of a substrate process system, according to one or more embodiments described and discussed herein.

FIG. 1 shows a schematic illustration of a substrate process system 100 according to embodiments of the present disclosure. The system 100 includes a process chamber 102 that includes a processing region 104 that is fluidly coupled to a gas monitoring module 106 via a conduit 114. The conduit 114 includes one or more conduits of varying shapes and sizes. The gas monitoring module 106 facilitates one or more of forming, testing, adjusting, and deploying of a gas mixture of one or more gaseous components, each having a predetermined gas concentration, to the processing region 104. In one or more examples, when it is determined that the gas mixture includes a target composition, which can be expressed as a function of a concentration of one gas in the mixture, the gas mixture is released from the gas monitoring module 106 into the processing region 104 of the process chamber 102. The process chamber 102 is electrically coupled to a power source 126 as well as a controller 124. The controller 124 is configured to execute a plurality of instructions that operate elements such as heaters in various locations in the chamber 102 or processing region 104, as well as to execute substrate process programs. A plurality of separate gas sources that can include a remote plasma source (not shown) can also be coupled to the process chamber 102.

The gas monitoring module 106 is coupled to a controller 118, a power source 116, a first gas source 120 and a second gas source 122. The second gas source 122 contains one or more gases or a gas mixture to be introduced into the processing region 104. The one or more gases of the second gas source 122 can be combined before or after entering the gas monitoring module 106. In one or more examples, the second gas source 122 is a gas box including a plurality of separate gas storage containers, each containing a gas of a different composition.

While the gas monitoring module 106 is shown herein as being associated with the separate power source 116 and a separate controller 118, in alternate embodiments, the process chamber 102 and the gas monitoring module 106 can share a controller and/or a power source. The gas monitoring module 106 includes a first cavity 108 coupled to the first gas source 120 via an inlet (not shown here). A second cavity 110 is thermally coupled to the first cavity 108 such that equilibrium in temperature is achieved between the two cavities 108 and 110. A wall 112 separates and is formed in between the first 108 and second 110 cavities. The wall 112 can have a thickness from 0.10 inches to 0.50 inches and be formed from or include stainless steel. In some examples, the first cavity 108 and the second cavity 110 may be spaced apart from one another, and independent temperature control and monitoring hardware may be utilized to maintain the temperatures of the first cavity 108 and the second cavity 110 within a predetermined range of one another.

The second cavity 110 of the gas monitoring module 106 is fluidly coupled to the second gas source 122 via an inlet (not shown here). The controller 118 is configured to execute a plurality of instructions to determine a concentration of a gas in a gas mixture in the second cavity 110. When the concentration of the gas is within a predetermined range or beyond a predetermined threshold, the gas mixture is released from the second cavity 110 into the processing region 104 of the process chamber 102. Each set of instructions is executed by the controller 118 to determine, adjust, reanalyze, and/or release the gas mixture from the gas monitoring module 106. In various embodiments, the instructions can include a process recipe for a gas flow rate and duration of gas flow into each of the first cavity 108 and second cavity 110. One or more transducers 128 are coupled to the gas monitoring module 106 and are configured to apply a plurality of sound pulses (e.g. acoustic waves) to the gas monitoring module 106. The sound pulse or sound pulses are applied to each of the first cavity 108 and the second cavity 110, including intensity and duration of the pulses, as well as a frequency of frequencies. In some examples, the instructions executed by the controller 118 further include parameters for adjustment of the gas mixture, including a type and a quantity of gas to add to the mixture to obtain a predetermined composition. The controller 118 also stores a predetermined concentration value, which can be a range or a threshold, upon which the release of the gas mixture in the second cavity 110 is predicated.

The second gas source 122 can contain a mixture of gases and can be configured as a plurality of storage units. Each storage unit contains one or more gases. Gases flowing from each storage unit may be mixed in a conduit (not shown) prior to reaching the second cavity 110, or mix inside of the second cavity 110. The second gas source 122 contains at least two gases, one of which is a common gas to the gas source 120. In some examples, an outlet (not shown) of the first cavity 108 is fluidly coupled to the second cavity 110 via an inlet (not shown) of the second cavity 110. In such examples, the gas from the gas source 120 flows through the first cavity 108 and then into the second cavity 110 to form part of the gas composition in the second cavity 110.

Figure 2:
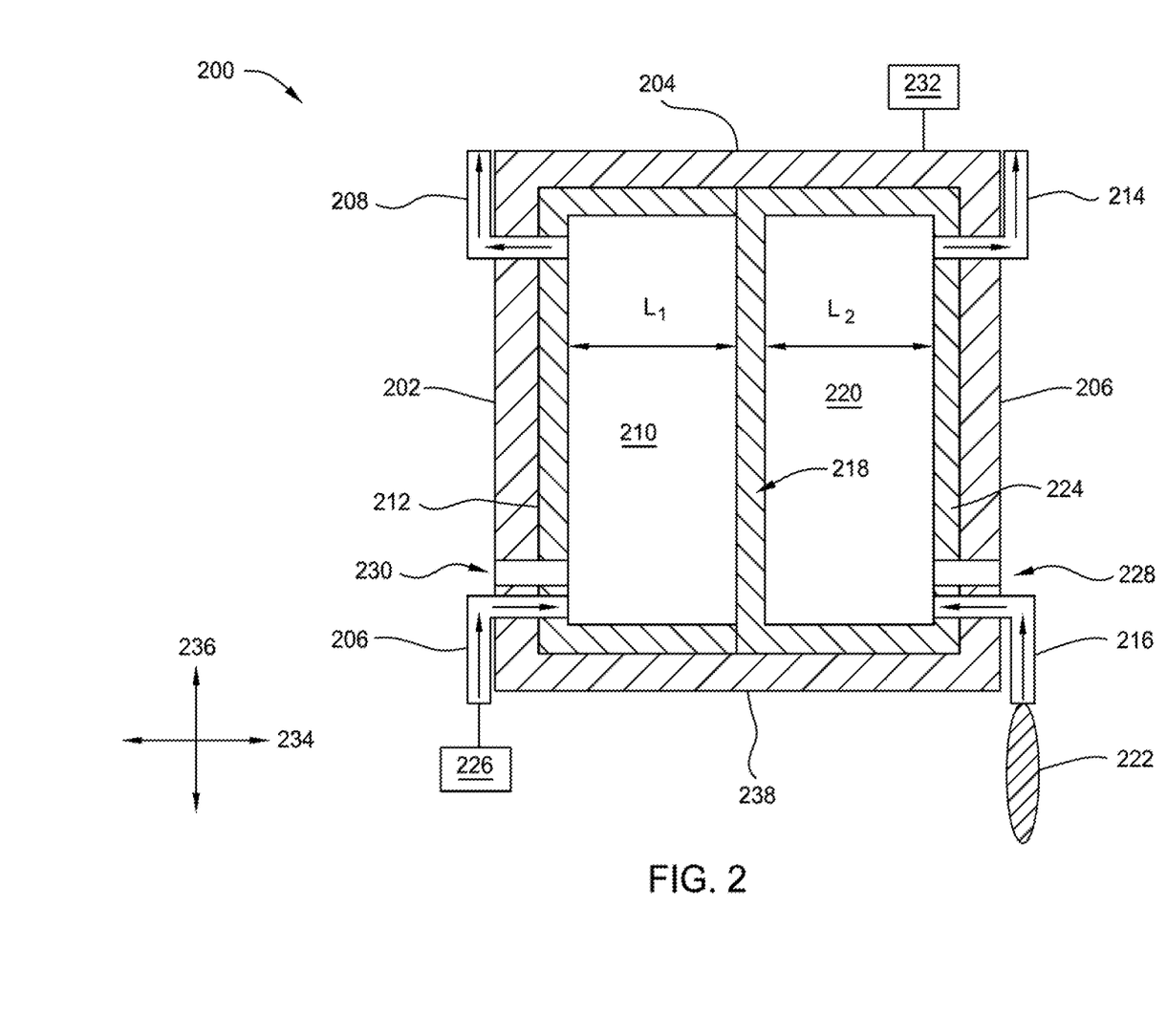
FIG. 2 shows a schematic cross-section of a gas monitoring module, according to one or more embodiments described and discussed herein.

FIG. 2 shows a schematic cross-section of a gas monitoring module 200 according to embodiments of the present disclosure. The gas monitoring module 200 in FIG. 2 may be similar to the gas monitoring module 106 discussed in FIG. 1. In one or more embodiments, the gas monitoring module 200 is defined in the cross-section in FIG. 2 by a first wall 202, a second wall 204, a third wall 206, and a fourth wall 238. The gas monitoring module 200 can have an outer wall 212 that can be fabricated from aluminum. The outer wall 212 encases an inner chamber 224 fabricated from stainless steel, quartz, nickel-based superalloy, or aluminum. A first cavity 210 is formed in the inner chamber 224 and is separated from a second cavity 220 in the inner chamber 224 by a wall 218. The wall 218 that separates the first cavity 210 from the second cavity 220 can be formed from a thermally conductive material, such as a metal, for example stainless steel. The wall 218 has a thickness of about 0.10 inches to about 0.50 inches. However, other sizes are contemplated. The first cavity 210 and the second cavity 220 are thermally coupled such that there is equilibrium in temperature between the two cavities 210 and 220. The equilibrium temperature depends on the embodiment and may or may not be known in order to determine the gas mixture composition as discussed herein.

In one or more embodiments, the first cavity 210 includes an inlet 206 and an outlet 208. The outlet 208 can be coupled to an exhaust container (not shown) or to the process chamber (e.g., such as the process chamber 102 in FIG. 1). The inlet 206 can be fluidly coupled to a gas source 226 that includes oxygen, hydrogen, or nitrogen gas. In some examples, the outlet 208 of the first cavity 210 is fluidly coupled (not shown here) to an inlet 216 of the second cavity 220, such that the gas from the first cavity 210 can be transferred to the second cavity 220. The second cavity 220 includes the inlet 216 and an outlet 214. The coupling of a second gas source (not shown in FIG. 2) to the second cavity 220 can occur directly at the inlet 216 of the second cavity 220, or via an ampule 222 or other device coupled to the inlet 216. The ampule 222 or other device coupled to the inlet 216 may be configured to introduce at least one gas in the second cavity 220 that is not the same as the gas in the first cavity 210. In some examples, during operation of the gas monitoring module 200, a first gas flows continuously through the first cavity 210 while a gas mixture, which includes a second gas and the first gas, flows continuously through the second cavity 220. The continuous flows of the first gas and the gas mixture are introduced into the process chamber. In other examples, during operation of the gas monitoring module 200, the gas mixture provided to the second cavity 220 continuously flows into the process chamber. In some examples, during operation of the gas monitoring module 200, the first gas continuously flows through the first cavity 210 into the second cavity 208 to facilitate formation of the gas mixture within the second cavity 208, and the gas mixture is continuously flowed into the process chamber from the second cavity 208.

A first thermocouple 230 is positioned in the outer wall 212 at a first location and is exposed to the first cavity 210 to measure a temperature within the first cavity 210. Similarly, a second thermocouple 228 is positioned within the outer wall 212 at a second location, and is used to measure the temperature of the cavity 220. The positions of the thermocouples 230, 228 are illustrative. In various embodiments, thermocouples 230, 228 may each be located in other areas of each of the first cavity 210 and the second cavity 220, depending upon the cavity size(s), geometries, and other factors. A length $L_1$ of the first cavity 210 is the same as a length $L_2$ of the second cavity 220. While $L_1$ and $L_2$ are shown here as being parallel to an axis 234 that is parallel to the module 200, in alternate embodiments, the effective lengths $L_1$, $L_2$ may be measured perpendicular to a normal plane (e.g., perpendicular to axis 234 and axis 236). For example, the effective lengths $L_1$, $L_2$ may be measured perpendicular to a normal plane if a transducer or other device is generating sound along an axis 236 perpendicular to the normal plane. A controller 232 is configured to communicate a plurality of instructions to the module 200 that include instructions on gas inlet and outlet flow rates in either or both of the first cavity 210 and the second cavity 220, temperature control of one or both cavities, or other factors.

Figure 3:
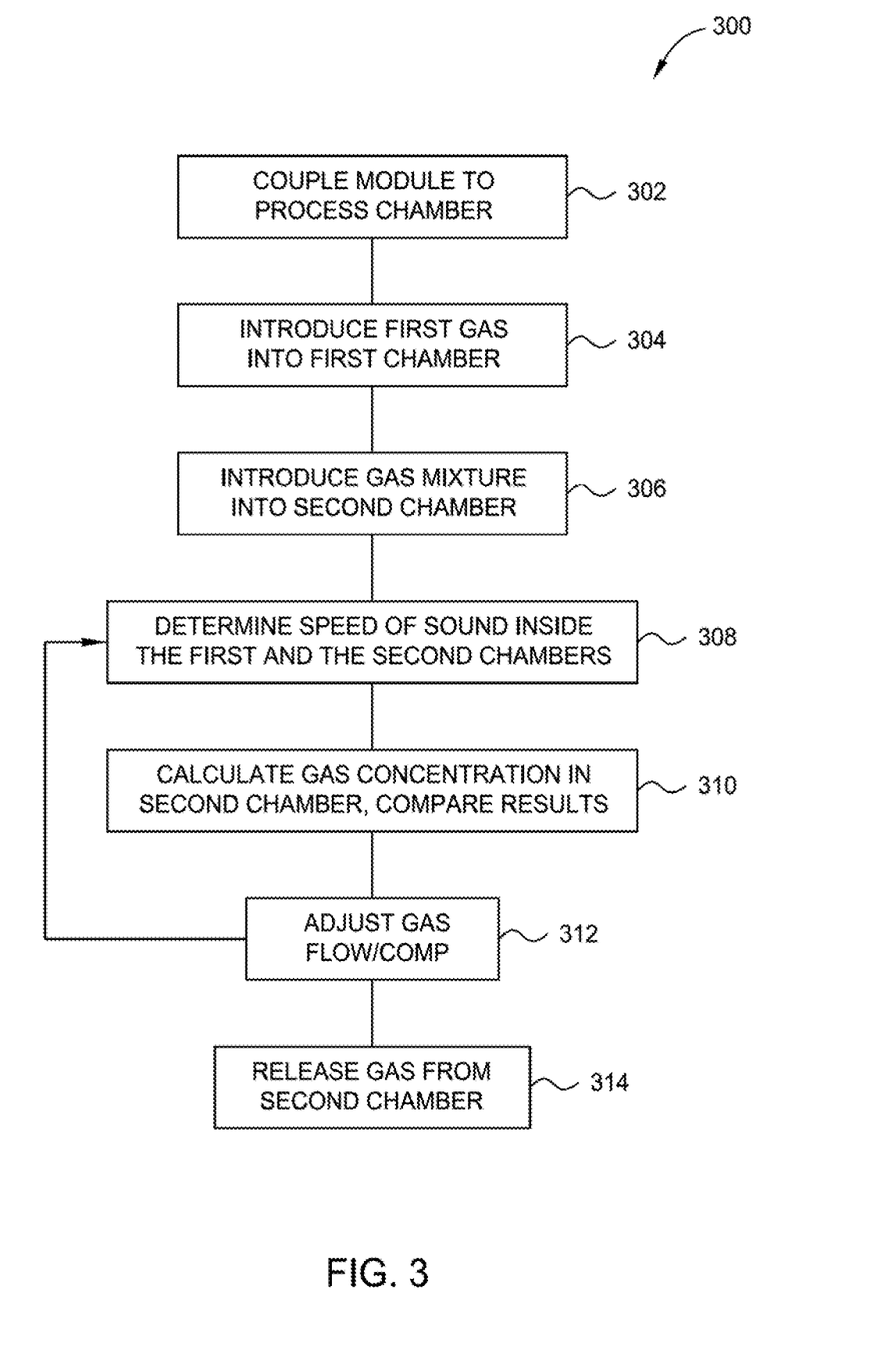
FIG. 3 is a method of determining a gas composition, according to one or more embodiments described and discussed herein.

FIG. 3 is a method 300 of determining a gas composition according to embodiments of the present disclosure. In the method 300, at optional operation 302, a gas monitoring module is removably coupled to a process chamber such that the module can be removed and reattached to the chamber or to other chambers after use. Alternatively, the gas monitoring module may be pre-installed at an original equipment manufacturer (OEM), and as such, operation 302 may not be part of method 300 in some embodiments. At operation 304, subsequent to operation 302, a first gas is introduced to a first cavity of the gas monitoring module. The first gas is introduced to the first cavity at operation 304 at a flow rate of about 10 sccm to about 100,000 sccm, or from about 100 sccm to about 5,000 sccm, or another flow rate, and may be introduced as a continuous flow to purge the first cavity and reduce impurities. At operation 306, which can occur before, during, after, or in a partially overlapping fashion with operation 304, a gas mixture is introduced into the second cavity. The gas mixture introduced into the second cavity has a composition that includes the first gas plus at least one additional gas. The gas mixture is introduced into the second cavity at operation 306 at a flow rate of about 1 sccm to about 10,000 sccm, or from about 50 sccm to about 1,000 sccm. However, other flow rates are also contemplated. The gas mixture can be introduced via a main inlet of the second cavity. The main inlet is fluidly coupled to multiple gas sources, of which at least two gas sources are employed to form the gas mixture in the second cavity. In that example, each gas source can be introduced into the second cavity at a flow rate from about 1 sccm to about 10,000 sccm, or another flow. Each gas source can flow gas into the second cavity at a different rate. In one or more examples, the first cavity contains hydrogen ($H_2$) or nitrogen ($N_2$) The gas mixture in the second cavity contains the gas of the first cavity (e.g., $H_2$ or $N_2$) and a second gas, such as phosphine ($PH_3$). The second cavity (220 as shown in FIG. 2) is shown as having a single inlet, but it is contemplated that the second gas source can house multiple storage devices that may each be configured with a separate respective inlet into the second cavity (220).

At operation 308, a speed of sound is determined inside of each of the first and second cavities by applying a sound pulse to each cavity. In one or more examples, an effective length ($L_{eff}$) of each of the first and second cavities is known (or is determined) and is equal, as is the temperature of the first and second cavities. The temperature can be near room temperature, measured by one or more thermocouples, or heated or chilled to a value from −40° C. to 60° C. In some examples, the $L_{eff}$ of the cavities is unknown and the temperature is also unknown but equal.

Using embodiments of the systems and methods discussed herein, a binary gas concentration or a gas mixture composition in a gas monitoring module is determined using the speed of sound. The speed of sound in ideal gas ($c_{ideal}$) is given by equation (1)

$$c_{ideal} = \sqrt{\gamma \cdot \frac{p}{\rho}} = \sqrt{\frac{\gamma \cdot R \cdot T}{M}} = \sqrt{\frac{\gamma \cdot k \cdot T}{m}}, \tag{1}$$

where γ is a heat capacity ratio of the ideal gas, R is a molar gas constant, k is the Boltzmann constant, ρ is the density of the gas, T is a temperature of the gas or gases in a vessel, m is the mass of the molecules of the gas, and M is the molar mass of the gas in the vessel. In an example of a binary gas mixture, γ and M can be calculated from the gas's corresponding properties. In another example of a binary mixture of gases that have a known γ and M, the concentration of both gases in the gas mixture can be calculated from a speed of sound measurement using a known T.

The speed of sound can be further measured in a given cavity using a sensor configured to detect a pulse of sound or a plurality of pulses of sound applied to a binary gas mixture in a cavity. The speed of sound (v) can be expressed as the length of the cavity (L) over the change in time between a time the pulse of sound was sent and a time when the pulse of sound was received, as shown in equation (2).

$$v = L/(t_{received} - t_{sent}) = L/\Delta L \tag{2}$$

Thus, the resonance in a cavity would occur at a frequency (f) shown in equation 3, $$f = nv/2L \tag{3}$$

where v is the speed of sound and n is a known harmonic. The frequency is measured and L is known, so v can be derived.

Resonance can also be used to determine a binary gas composition by scanning the frequency and locating the resonance of the harmonics n and n+1. When an effective length $L_{eff}$ is known, the speed of sound is determined. In some examples, the v can be known, for example, because a gas such as $H_2$ or $N_2$ has a known value for v at a known temperature. The $L_{eff}$ can then be determined. A resonance frequency is a frequency at which the response amplitude is at a relative maximum. Using the resonance methods according to embodiments of the present disclosure, a transducer coupled to one or more cavities increases and decreases in sound frequency and detects power spikes. The power spikes are then used to determine which frequencies are the resonance frequencies of the cavity.

In one or more embodiments, a gas composition is measured using sound resonance in a gas monitoring module that includes two thermally coupled cavities. A first cavity contains a first gas, and a second cavity contains the first gas and a second gas, forming a gas mixture. When the cavity lengths (L) are known, measuring the speed of sound inside the first cavity containing the first gas enables the calculation of the temperature (T), for example, using equation (1). The length L can also be referred to as the effective length $L_{eff}$ and is measured in the direction in which the sound pulses are applied. Once the T is determined and a speed of sound in the second cavity is known as well as an M and a γ of each of the first gas and the second gases, the concentration of the first and second gases in the second cavity can be determined. In one or more examples, the speed of sound in the first cavity is measured by determining the frequencies of the first (n) and second (n+1) harmonics.

Equations (4)-(6) illustrate a multi-frequency resonance calculation for $f_1$, $f_2$, and $f_3$, where each of $f_1$, $f_2$, and $f_3$, is resonant with the same m and n values but with a different l value, where l represents a harmonic.

$$f_1 = \frac{v}{2}\sqrt{\left(\frac{\ell}{L_x}\right)^2 + \left(\frac{m}{L_y}\right)^2 + \left(\frac{n}{L_z}\right)^2} \quad (4)$$

$$f_2^2 - f_1^2 = \frac{v^2}{4}\left(\left(\frac{l+1}{L_{eff}}\right)^2 - \left(\frac{l}{L_{eff}}\right)^2\right) \quad (5)$$

$$f_3^2 - f_1^2 = \frac{v^2}{4}\left(\left(\frac{l+2}{L_{eff}}\right)^2 - \left(\frac{l}{L_{eff}}\right)^2\right) \quad (6)$$

In embodiments discussed herein that employ the gas monitoring module, an M of the gas mixture can be calculated as in the example below even if an effective length ($L_{eff}$) is unknown. The effective length is a length measured in the same direction as the sound pulses are applied to the cavities, and pulses are applied to each cavity separately. In one or more examples, each cavity of the gas monitoring module has the same $L_{eff}$. In other embodiments, each cavity may have a different length. As shown in the equation (7) below, frequencies are calculated for the first and second harmonics for the first cavity that contains a single gas.

$$f_{2H}^2 - f_{1H}^2 = \frac{v^2}{4}\left(\left(\frac{n+1}{L_{eff}}\right)^2 - \left(\frac{n}{L_{eff}}\right)^2\right) = \frac{\gamma_H RT}{4M_H}\left(\left(\frac{n+1}{L_{eff}}\right)^2 - \left(\frac{n}{L_{eff}}\right)^2\right) \quad (7)$$

Similarly, frequencies are calculated for the first and second harmonics for the second cavity that contains a gas mixture including the gas of the first cavity. An example calculation is shown in equation (8) below where "n" is the harmonic.

$$f_{2mix}^2 - f_{1mix}^2 = \frac{v^2}{4}\left(\left(\frac{n+1}{L_{eff}}\right)^2 - \left(\frac{n}{L_{eff}}\right)^2\right) = \frac{\gamma_{mix} RT}{4M_{mix}}\left(\left(\frac{n+1}{L_{eff}}\right)^2 - \left(\frac{n}{L_{eff}}\right)^2\right) \quad (8)$$

Subsequent to the execution of the calculations in equations (5) and (6), which can occur in series, in parallel, or in an otherwise overlapping fashion, a ratio of the difference between the frequencies of the first and the second harmonics is used to determine the molar weight of the gas mixture in the second cavity ($W_{mix}$). An example ratio calculation is shown in equation (9) below.

$$\frac{f_{2H}^2 - f_{1H}^2}{f_{2mix}^2 - f_{1mix}^2} = \frac{\gamma_H}{M_H}\frac{M_{mix}}{\gamma_{mix}} \quad (9)$$

Thus, the above calculation can be executed to determine the composition of the second cavity, for example, when there is a known v and the l (resonance mode in a given direction) and $L_{eff}$ can be determined. In equation (6), the n is a resonant mode, or harmonic number in a direction, an integer that indicates how many periods occur for that resonant.

Subsequently at operation 310, the gas concentration of the at least one additional gas in the second cavity is determined based upon the calculations at operation 308. Because the second cavity has a gas mixture of at least two gases, one gas which is also present in the first cavity, the concentration of the second gas in the gas mixture in the second cavity is determined at operation 310 using the known molar mass of the first gas present in the first cavity and the molar mass of the gas mixture in the second cavity. Further at operation 310, a comparison of the concentration of the second gas and a threshold or a range of compositions is made. In one or more examples, executable instructions associated with operation 310 contain a range of composition (e.g., X %-Y %) for the second gas in the gas mixture in the second cavity. In some examples, the executable instructions include a predetermined threshold that is either a maximum or a minimum value for the concentration of the second gas in the second cavity. The comparison is made at operation 310 to determine if the gas mixture of the second cavity is to be released, adjusted, and/or reanalyzed in operations discussed below.

In one or more examples, subsequent to and based on the comparison at operation 310, if the comparison determines that the calculated gas composition is not within the range or the threshold, the gas flow rate in the second cavity can be adjusted (increased or decreased) for one or more gases of the gas mixture at operation 312. In one or more embodiments, the adjustment to the flow rate of the one or more gases in the gas mixture in the second cavity at operation 312 can be executed automatically, for example, by one or more controllers coupled to the system 100 discussed in FIG. 1. In one or more embodiments, a first gas and a second gas are separately flowed into the second cavity and mixed in the second cavity. The flow rate of the first gas and the flow rate of the second gas can be independently adjusted at operation 312. In one or more examples, a gas flow rate and a gas flow time are adjusted at operation 312 as long as the cavity is not over-pressurized. For a continuous flow embodiment where the gas mixture composition is determined while the gas mixture is flowing through the second cavity, as opposed to being mixed in the second cavity prior to release, a flow rate adjustment may similarly be used at operation 312.

In some examples, the adjustment at operation 312 can include adjusting a gas flow time or a gas flow rate of one or both gases of the gas mixture. In some examples, operations 308 and 310 are repeated at least one time to achieve a desired composition of the gas mixture in the second cavity. Once the gas mixture in the second cavity reaches a desired composition, then the gas mixture in the second cavity is released into the process chamber at operation 314.

Alternatively, it is contemplated that operation 312 may be omitted, and operation 310 may proceed directly to operation 314. The release of the gas mixture at operation 314 may include releasing the gas mixture at a variable flow rate from about 1 sccm to about 5,000 sccm, or from about 100 sccm to about 500 sccm, or another flow rate. In one or more embodiments, the process chamber coupled to the gas monitoring module can be held at a predetermined pressure and temperature which can be the same as or different from the pressure and temperature of the second cavity of the gas monitoring module.

Figure 4:
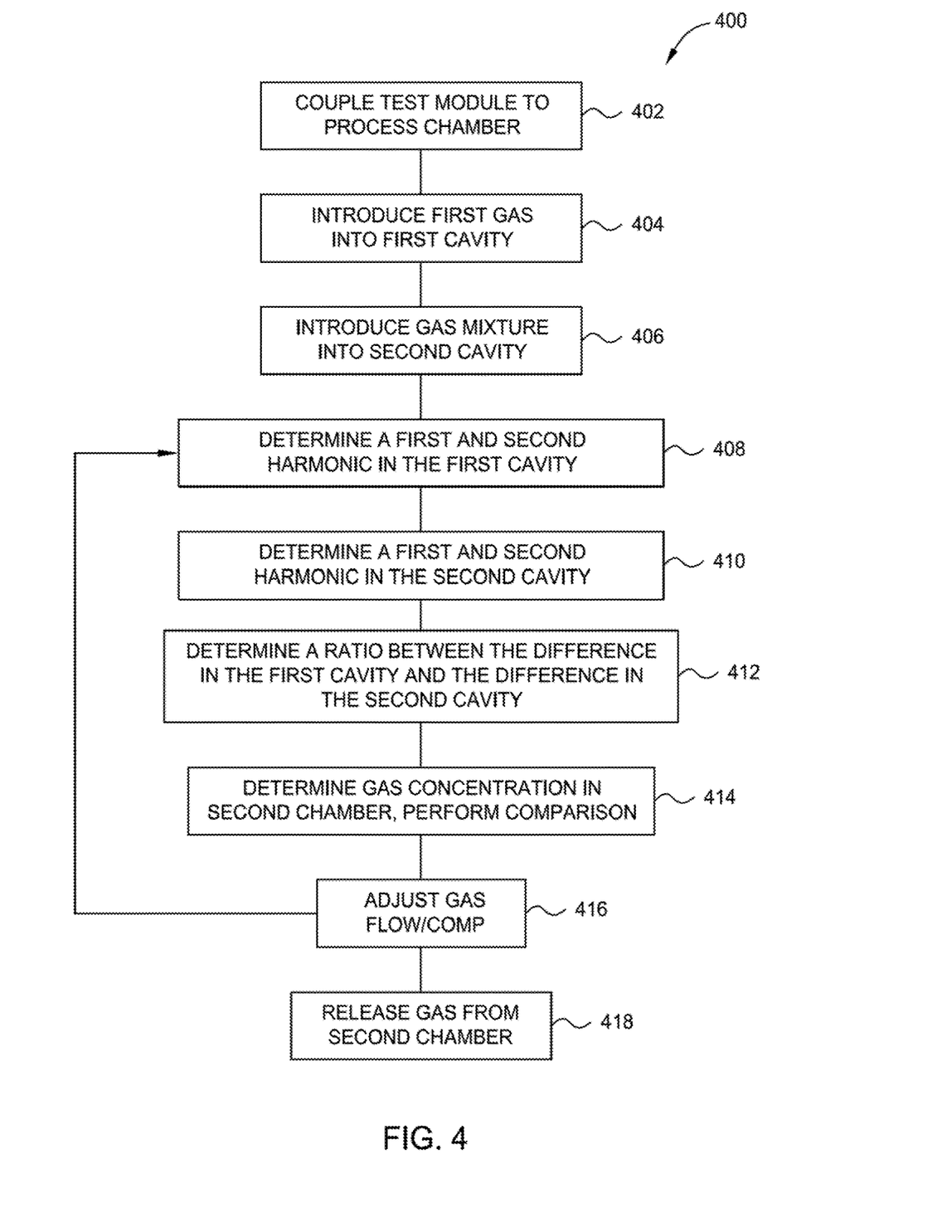
FIG. 4 is a method of determining a gas composition, according to one or more embodiments described and discussed herein.

FIG. 4 is a method 400 of an embodiment of determining a gas composition according to embodiments of the present disclosure. In the method 400, at operation 402, a gas monitoring (test) module is removably coupled to a process chamber such that the module can be removed and reattached to the chamber or to other chambers after use. Alternatively, the gas monitoring module may be coupled to the process chamber by an OEM or other party, and therefore, may be omitted from method 400. At an operation 404, subsequent to operation 402, a first gas is introduced to a first cavity of the gas monitoring module. The first gas can be introduced at a flow rate of about 10 sccm to about 100,000 sccm, or from about 100 sccm to about 5,000 sccm, or other flow rate. The first gas may be introduced as a continuous flow to purge the first cavity and reduce impurities. At operation 406, which can occur before, during, after, or in a partially overlapping fashion with operation 404, a gas mixture is introduced into the second cavity that contains the gas of the first cavity (e.g., the first gas) plus at least one additional gas. In one or more embodiments, the gas mixture is introduced into the second cavity at operation 406 at a flow rate of about 1 sccm to about 10,000 sccm, or from about 50 sccm to about 1,000 sccm, or another flow rate. The gas mixture can be introduced via a plurality of inlets such that a main inlet of the second cavity. The main inlet is fluidly coupled to multiple gas sources, of which at least two gas sources are employed to form the gas mixture in the second cavity. In one or more examples, the gas in the first cavity contains hydrogen ($H_2$) or nitrogen ($N_2$) and the gas mixture in the second cavity contains the gas of the first cavity (e.g., $H_2$ or $N_2$) plus phosphine ($PH_3$).

Further in the method 400, at operation 408, a frequency of a first harmonic of the gas in the first cavity and a frequency of a second harmonic of the gas in the first cavity are determined. At operation 410, a frequency of a first harmonic of the gas mixture in the second cavity and a frequency of a second harmonic of the gas mixture in the second cavity are each determined. The operations 408 and 410 can be executed, for example, by one or more processors discussed in FIG. 1, simultaneously, sequentially, or in a partially overlapping fashion. When executed sequentially, either operation 408 or operation 410 can be executed first.

At operation 412, subsequent to operations 408 and 410, a ratio between the calculated harmonics is determined. This ratio determined at operation 412 includes a ratio between the difference between the first and second harmonics in the first cavity and the first and second harmonics in the second cavity, and can be similar to the equation (6) discussed above. An M of each of the gas in the first cavity and the gas mixture can then be determined. A concentration of the second gas in the gas mixture in the second cavity (e.g., the gas that is not in the first cavity), is determined at operation 414. Further at operation 414, a comparison of the concentration of the second gas and a threshold or a range of compositions is performed. In one or more examples, executable instructions associated with operation 414 contain a range of composition (e.g., X %-Y %) for the second gas in the gas mixture in the second cavity, and in other examples, the executable instructions include a predetermined threshold that is either a maximum or a minimum value for the concentration of the second gas in the second cavity. The comparison is made at operation 414 to determine if the gas mixture of the second cavity is to be released, adjusted, and/or reanalyzed, as discussed in detail below.

In one or more examples, subsequent to operation 414, the gas flow in the second cavity is adjusted at operation 416 based upon the calculation and comparison at operation 414. The gas flow in the second cavity is adjusted at operation 416 by adjusting a flow rate of the first gas, a flow rate of the second gas, a flow time of the first gas or the second gas, a flow rate of the gas mixture, and/or a flow time of the gas mixture. The adjustment at operation 416 is executed automatically, for example, by one or more controllers coupled to the system 100 discussed in FIG. 1. In embodiments where there is a continuous flow from the second cavity into the process chamber, the adjustments at operation 416 occur during this continuous flow.

In some examples, subsequent to the calculation and comparison at operation 414, the gas flow in the second cavity is adjusted at operation 416 based upon the calculation and comparison at operation 414. In this example, subsequent to the adjustment at operation 416, operations 408-414 are repeated in one or more iterations until the comparison at operation 414 indicates that the gas concentration of the second gas in the second cavity is within the predetermined range or meets the predetermined threshold. Once the gas mixture in the second cavity is adjusted to the predetermined concentration or threshold, the gas mixture in the second cavity is released into the process chamber at operation 418. In another embodiment, it is contemplated that operation 418 may be performed after operation 414, omitting operation 416

While the gas monitoring modules discussed herein includes two cavities and are directed towards examples of determining a concentration of a gas in a binary mixture, in alternate embodiments, three or more cavities may be used, and single, binary, tertiary, or other gas mixtures are used in order to determine a composition of the gas mixture (e.g., a concentration of one or more gases in a gas mixture).

The systems and methods provide a safe, efficient, accurate, and dynamic method of determining a concentration of a gas in at least a binary mixture, and facilitate adjustment of the gas mixture and release of the gas mixture from a gas monitoring module into a process chamber.

In one or more embodiments, a gas monitoring module includes a plurality of cavities. A first cavity of the plurality of cavities contains a known gas concentration and a second cavity of the plurality of cavities contains a plurality of gases including the known gas of the first cavity. By determining a speed of sound in the first cavity and then the second cavity, the composition of the gas mixture in the second cavity, and, thus, a concentration of at least a second gas of the gas mixture in the second cavity are determined. In one or more examples, if it is determined using the systems and methods discussed herein that a concentration of the second gas in the second cavity is within a predetermined range or meets a predetermined threshold, the gas mixture in the second cavity is released into the process chamber. In some examples, if it is determined that the concentration is outside of a predetermined range or does not meet a predetermined threshold, a flow of one or more gases of the mixture is adjusted in response to the determination. In some embodiments, the adjusted mixture of the second cavity is released automatically subsequent to the adjustment, and in alternate embodiments, the concentration calculation can be repeated prior to releasing the gas mixture into the process chamber. In still other embodiments, the concentration is measured during a continuous flow of the gas mixture into the process chamber and the flow rate from the second cavity and/or the flow rate from the first cavity and the second cavity into the process chamber can be adjusted.

In one or more embodiments, a gas mixture containing a carrier gas can be made, tested, or adjusted, and then released. The gas mixture includes two different gases, that is, gases of different elemental compositions. In another embodiment, a continuous flow embodiment, the gas mixture is tested as discussed herein and adjusted as needed during a continuous flow of the gas mixture into the process chamber. In one or more examples, an adjustment of the gas mixture in the second cavity can be based on the concentration of the gas mixture determined as discussed herein. An adjustment of the gas mixture flow in the second cavity can be made such that a flow rate multiplied by a concentration in order to meet target flow rate (measured in sccm) for delivery of the gas mixture to the process chamber. In this example, a carrier flow rate can be calculated as the flow rate of the gas mixture×(c), where c is the concentration of the carrier gas in the gas mixture. The carrier gas flow rate in the first cavity can be adjusted such that the sum of the carrier flow rates in each cavity meet the target carrier flow rate. Thus, in one or more embodiments, the two flows of gas through both cavities will be merged after each flow exits the gas monitoring module and the merged gas flow is sent to the process chamber.

To facilitate understanding, identical reference numerals have been used, where possible, to designate identical elements that are common to the figures. It is contemplated that elements and features of one embodiment may be beneficially incorporated in other embodiments without further recitation.

While the foregoing is directed to embodiments of the present disclosure, other and further embodiments of the disclosure may be devised without departing from the basic scope thereof, and the scope thereof is determined by the claims that follow.

What is claimed is:

1. A method of determining a gas composition in a process chamber, comprising:
    introducing a first gas into a first cavity of a gas monitoring module, wherein the first cavity of the gas monitoring module is thermally coupled to a second cavity of the gas monitoring module, wherein the first cavity comprises a first outlet and a first inlet and the first gas is introduced via the first inlet;
    introducing a gas mixture comprising the first gas and a second gas into a second cavity of the gas monitoring module, wherein the second cavity comprises a second inlet and a second outlet and the gas mixture is introduced via the second inlet;
    determining a first speed of sound inside the first cavity;
    determining a second speed of sound inside the second cavity; and
    determining a concentration of the second gas in the second cavity based on the first speed of sound and the second speed of sound.

2. The method of claim 1, further comprising, during the determining of the first speed of sound and the second speed of sound, continuously flowing the gas mixture from the second cavity to a process chamber.

3. The method of claim 1, further comprising, prior to determining the second speed of sound, transferring a portion of the first gas from the first cavity into the second cavity via the first outlet of the first cavity and the second inlet of the second cavity.

4. The method of claim 3, further comprising, subsequent to the transferring, determining a concentration of the first gas in the second cavity and a second concentration of the second gas in the second cavity.

5. The method of claim 1, wherein the first gas comprises hydrogen ($H_2$) or nitrogen ($N_2$).

6. The method of claim 1, wherein the first cavity has a first length that is equal to a second length of the second cavity.

7. The method of claim 6, wherein determining the speed of sound in the first cavity and determining the speed of sound in the second cavity each comprises transmitting pulses in a shared direction of the first and the second lengths.

8. The method of claim 6, wherein the first inlet and the second inlet are spaced equidistant from a wall that fluidly isolates the first cavity from the second cavity.

9. The method of claim 1, further comprising:
    comparing the determined concentration of the second gas to a predetermined range, and based on the comparison:
        releasing the gas mixture from the second cavity into the process chamber when the comparison determines that the concentration is within the predetermined range; or
        adjusting the gas mixture in the second cavity when the comparison determines that the concentration is outside of the predetermined range.

10. The method of claim 9, further comprising, subsequent to adjusting the gas mixture, releasing the gas mixture from the second cavity into the process chamber.

11. A method of determining a gas composition in a process chamber, comprising:
    coupling a device to a process chamber, wherein a first cavity of the device is thermally coupled to a second cavity of the device and the first cavity and second cavity are at a first temperature, wherein the first cavity comprises a first outlet and a first inlet and the second cavity comprises a second outlet and a second inlet;
    introducing a first gas into the first cavity via the first inlet;
    introducing a gas mixture comprising the first gas and a second gas into the second cavity via the second inlet;
    determining a first difference between a frequency of a first harmonic and a frequency of the second harmonic of the first gas;
    determining a second difference between a frequency of a first harmonic and a frequency of the second harmonic of the gas mixture; and based on a ratio of the first difference to the second difference, determining a concentration of the second gas in the second cavity.

12. The method of claim 11, wherein determining the concentration of the second gas in the second cavity comprises determining, based on the ratio, a molar mass of the gas mixture and a heat capacity of the gas mixture and a molar mass of the first gas and a heat capacity of the first gas.

13. The method of claim 11, further comprising establishing a continuous flow of the gas mixture from the second cavity into the process chamber.

14. A system comprising:
a gas monitoring module comprising an outside wall and an interior wall, wherein the interior wall forms a first cavity having a first inlet and a first outlet and a second cavity of the gas monitoring module comprising a second inlet and a second outlet, wherein the first cavity and the second cavity are thermally coupled;
a first thermocouple associated with the first cavity; and
a second thermocouple associated with the second cavity.

15. The system of claim 14, wherein the first cavity, the second cavity, and the wall are fabricated from stainless steel.

16. The system of claim 14, further comprising:
a plurality of logic stored in a storage media and executable by a controller to:
release the first gas from the first gas source into the first cavity for one of a predetermined time period or at a predetermined gas flow rate;
release the gas mixture from the second gas source into the gas cavity for one of a predetermined time period or at a predetermined gas flow rate;
determine a first speed of sound inside the first cavity;
determine a second speed of sound inside the second cavity; and
based on the first speed of sound and the second speed of sound, determine a concentration of the second gas in the second cavity.

17. The system of claim 16, further comprising the plurality of logic configured to, when executed by the controller:
compare the determined concentration of the gas mixture in the second cavity to a predetermined range;
release, based on the comparison, the gas mixture into a process chamber coupled to the second cavity via a conduit and via the second outlet, when the determined concentration is within the predetermined range; or
adjust, based on the comparison, a concentration of at least one component of the gas mixture.

18. The system of claim 14, further comprising:
the first cavity defined by the wall, a first top surface, a first bottom surface parallel to the top surface, and a first outside wall parallel to the first wall;
the second cavity defined by the wall, a second top surface, a second bottom surface parallel to the top surface, and a second outside wall parallel to the first wall, wherein a central axis is defined along the wall, wherein the first inlet and the second inlet are equidistant from the central axis, and wherein the first outlet and the second outlet are equidistant from the central axis.

19. The system of claim 14, further comprising
a first gas source coupled to the first inlet and comprising a first gas;
a second gas source coupled to the second inlet, wherein the second gas source comprises a gas mixture; and
a central axis defined parallel to the wall, wherein a location of the first inlet and a location of the first outlet in the first cavity are mirrored across the central axis by a location of the second inlet and a location of the second outlet.

20. The system of claim 14, wherein the second cavity is fluidly coupled to a process chamber via a conduit of the process chamber and the second outlet of the second cavity.

* * * * *